US008088751B2

(12) United States Patent
Suh et al.

(10) Patent No.: US 8,088,751 B2
(45) Date of Patent: Jan. 3, 2012

(54) PHARMACEUTICAL COMPOSITION FOR TREATING DEMENTIA COMPRISING SHRNA INHIBITING S100A9 EXPRESSION

(75) Inventors: Yoo-Hun Suh, Seoul (KR); Keun-A Chang, Seoul (KR)

(73) Assignee: SNU R&DB Foundation, Nakseongdae-dong, Gwanak-gu, Seoul (KR)

( * ) Notice: Subject to any disclaimer, the term of this patent is extended or adjusted under 35 U.S.C. 154(b) by 0 days.

(21) Appl. No.: 12/851,273

(22) Filed: Aug. 5, 2010

(65) Prior Publication Data

US 2011/0294866 A1 Dec. 1, 2011

(30) Foreign Application Priority Data

May 31, 2010 (KR) ........................ 10-2010-0050864

(51) Int. Cl.
*A61K 48/00* (2006.01)
(52) U.S. Cl. ..................................................... 514/44 R
(58) Field of Classification Search .................. 514/44 R
See application file for complete search history.

(56) References Cited

OTHER PUBLICATIONS

ISN/APSN 2009, 22nd Biennial Meeting of the International Society for Neurochemistry, Program Book, Busn Korea, Aug. 23-28, 2009 BEXCO.
"TH06 Molecular mechanisms involved in neuropathologies", Journal of Neurochemistry, vol. 110, Supplement 2, p. 180, Sep. 2009.
Tae-Young Ha et al., "S100a9 Knockdown Decreases the Memory Impairment and the Neuropathology in Tg2576 Mice, AD Animal Model", Plos ONE, Jan. 2010, vol. 5, Issue 1, pp. 1-11.

*Primary Examiner* — Jon E Angell
(74) *Attorney, Agent, or Firm* — Robert E. Bushnell, Esq.

(57) ABSTRACT

Disclosed is a composition for treating dementia including shRNA to inhibit expression of S100a9. More particularly, the present disclosure describes a composition for prevention or treatment of dementia which includes shRNA having a nucleotide sequence defined by SEQ. ID No. 1 or 2 or a mixture thereof wherein the nucleotide sequence is complementarily bonded to mRNA of S100a9 in order to inhibit expression of S100a9, as well as a method for prevention or treatment of dementia, including administering the foregoing shRNA into a mammalian cell including a human cell or in vitro established mammalian cell-line, in order to inhibit expression of S100a9 protein.

6 Claims, 12 Drawing Sheets

FIG. 4A

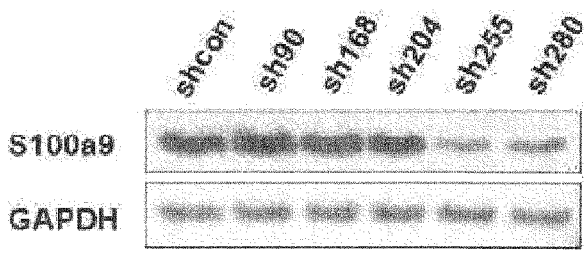

FIG. 4B

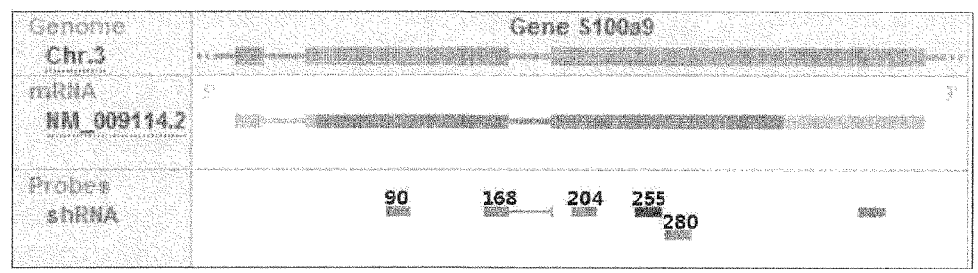

sh90: CCGGCTTCCATCAATACTCTAGGAACTCGAGTTCCTAGAGTATTGATGGAAGTTTTTG
sh168: CCGGGTTGGCAACCTTTATGAAGAACTCGAGTTCTTCATAAAGGTTGCCAACTTTTTG
sh204: CCGGCTGATGGCAAAGTTGATCTTTCTCGAGAAAGATCAACTTTGCCATCAGTTTTTG
sh255: CCGGGCTGAGCTTTGAGGAGTGTATCTCGAGATACACTCCTCAAAGCTCAGCTTTTTG
sh280: CCGGCTGATGGCAAAGTTGATCTTTCTCGAGAAAGATCAACTTTGCCATCAGTTTTTG

SEQUENCE LISTING

```
<160> NUMBER OF SEQ ID NOS: 11

<210> SEQ ID NO 1
<211> LENGTH: 58
<212> TYPE: DNA
<213> ORGANISM: Artificial Sequence
<220> FEATURE:
<223> OTHER INFORMATION: sh255

<400> SEQUENCE: 1
ccgggctgag ctttgaggag tgtatctcga gatacactcc tcaaagctca gcttttg       58

<210> SEQ ID NO 2
<211> LENGTH: 58
<212> TYPE: DNA
<213> ORGANISM: Artificial Sequence
<220> FEATURE:
<223> OTHER INFORMATION: sh280

<400> SEQUENCE: 2
ccggctgatg gcaaagttga tctttctcga gaaagatcaa ctttgccatc agtttttg      58

<210> SEQ ID NO 3
<211> LENGTH: 20
<212> TYPE: DNA
<213> ORGANISM: Artificial Sequence
<220> FEATURE:
<223> OTHER INFORMATION: S100a9 forward primer

<400> SEQUENCE: 3
cagcataacc accatcatcg                                                20

<210> SEQ ID NO 4
<211> LENGTH: 20
<212> TYPE: DNA
<213> ORGANISM: Artificial Sequence
<220> FEATURE:
<223> OTHER INFORMATION: S1009 reverse primer
```

```
<400> SEQUENCE: 4
gtcctggttt gtgtccaggt                                              20

<210> SEQ ID NO 5
<211> LENGTH: 20
<212> TYPE: DNA
<213> ORGANISM: Artificial Sequence
<220> FEATURE:
<223> OTHER INFORMATION: S100a9 forward primer

<400> SEQUENCE: 5
ccagatcatg tttgagacct                                              20

<210> SEQ ID NO 6
<211> LENGTH: 20
<212> TYPE: DNA
<213> ORGANISM: Artificial Sequence
<220> FEATURE:
<223> OTHER INFORMATION: S100a9 reverse primer

<400> SEQUENCE: 6
gttgccaata gtgatgacct                                              20

<210> SEQ ID NO 7
<211> LENGTH: 58
<212> TYPE: DNA
<213> ORGANISM: Artificial Sequence
<220> FEATURE:
<223> OTHER INFORMATION: Sh90

<400> SEQUENCE: 7
ccggcttcca tcaatactct aggaactcga gttcctagag tattgatgga agtttttg    58

<210> SEQ ID NO 8
<211> LENGTH: 58
<212> TYPE: DNA
<213> ORGANISM: Artificial Sequence
<220> FEATURE:
<223> OTHER INFORMATION: Sh168

<400> SEQUENCE: 8
ccgggttggc aacctttatg aagaactcga gttcttcata aaggttgcca actttttg    58

<210> SEQ ID NO 9
<211> LENGTH: 58
<212> TYPE: DNA
<213> ORGANISM: Artificial Sequence
<220> FEATURE:
<223> OTHER INFORMATION: Sh204

<400> SEQUENCE: 9
ccggctgatg gcaaagttga tctttctcga gaaagatcaa ctttgccatc agtttttg    58

<210> SEQ ID NO 10
<211> LENGTH: 58
<212> TYPE: DNA
<213> ORGANISM: Artificial Sequence
<220> FEATURE:
<223> OTHER INFORMATION: Sh255

<400> SEQUENCE: 10
ccgggctgag ctttgaggag tgtatctcga gatacactcc tcaaagctca gctttttg    58

<210> SEQ ID NO 11
<211> LENGTH: 58
```

-continued

```
<212> TYPE: DNA
<213> ORGANISM: Artificial Sequence
<220> FEATURE:
<223> OTHER INFORMATION: Sh280

<400> SEQUENCE: 11
ccggctgatg gcaaagttga tctttctcga gaaagatcaa ctttgccatc agtttttg      58
```

PHARMACEUTICAL COMPOSITION FOR TREATING DEMENTIA COMPRISING SHRNA INHIBITING S100A9 EXPRESSION

CLAIM OF PRIORITY

This application claims priority from Korean Patent Application No. 10-2010-50864, filed on May 31, 2010 in the Korean Intellectual Property Office, the entire disclosure of which is incorporated herein, by reference.

BACKGROUND OF THE INVENTION

1. Field of the Invention

The present invention relates to a pharmaceutical composition for prevention or treatment of dementia, which includes shRNA containing a nucleotide sequence of SEQ. ID No. 1 or 2 capable of inhibiting expression of S100a9, as well as a method for prevention or treatment of dementia by administering the foregoing shRNA into cells of mammals including, for example, human beings.

2. Description of the Related Art

It is known that S100a9 is an 5100 family as a calcium-binding protein associated with inflammation. Increase in activated S100a9 in microglia cells activates, signal transduction (or signaling) dependent on mitogen-activated protein kinase (MAPK) cascade, NF-kB or calcium.

Neurodegenerative diseases including cerebral ischemia and Alzheimer's disease have been known to associate with modified expression or function of S100 family members and, recently, S100a9 is known to participate in inflammation of patients with Alzheimer's disease and be considerably increased in neuritic plaques. However, a pathological mechanism regarding the foregoing conditions is still not disclosed.

RNA-mediated interference (RNAi) refers to a phenomenon that an RNA fragment with a size of 21 to 25 nucleotides (nt) is selectively bonded to mRNA having a complementary sequence and degrades the same in order to inhibit protein expression.

Since Elbashir research team reported in 2001 that expression of a particular gene may be selectively inhibited when a short dsRNA with 21 bases (siRNA) is introduced into a cultured mammal cell, applicability of RNAi in mammalian cells was noticeably increased. At present, gene expression inhibitory technologies using siRNA are generally used to understand functions of various genes and are being actively applied to development of drugs for treating incurable diseases such as cancer, infectious diseases, etc.

Induction of cell apoptosis in human myelogenous leukemia cells using siRNA specific to oncogenic genes such as Bcl-2 and c-Raf closely relating to tumor formation, was reported. It was also disclosed that using siRNA specific to Bcr-ab1 fused genes massively expressing in chronic myelogenous leukemia (CML) may remarkably reduce expression of Bcr-abl protein.

Alternatively, approaches for inhibition of viral infection using a complementary siRNA of CXCR4/CCR5RNA, which is a co-receptor of siRNA or HIV-1 complementary to HIV RNA, are being actively studied and developed. In recent years, it was reported that a synthesized siRNA complementary to hepatitis virus may effectively inhibit gene expression of the hepatitis virus.

Such techniques to inhibit expression of particular genes in animal cells using siRNA may include, for example, in vitro preparation of siRNA comprising synthesizing siRNA in vitro and introducing the same into cells. However, the foregoing method has disadvantages in that bio-synthesis of siRNA requires high costs and cell introduction of the synthesized siRNA has relatively low efficacy with regard to cell plasma infection, in turn entailing insufficient gene inhibition using siRNA while exhibiting RNAi effects for 2 to 3 days only. In order to overcome the above problems, a method of introducing a siRNA plasmid vector capable of expressing siRNA into cells was developed.

Especially, an siRNA plasmid vector expressing a short hairpin RNA (shRNA), wherein sense and anti-sense sequences of siRNA target sequence are located from a promoter of RNA polymerase III by interposing a loop having 5 to 9 bases, is characterized in that the shRNA expressed after introduction thereof into cells is transformed into siRNA by an siRNA processing enzyme (that is, Dicer or RNase III) and the transformed siRNA can selectively inhibit expression of specific genes.

SUMMARY OF THE INVENTION

In order to solve conventional problems described above, an object of the present invention is to provide a pharmaceutical composition for prevention and treatment of dementia, including shRNA with a specific sequence of RNA inhibiting expression of S100a9.

Another object of the present invention is to provide a method of inhibiting expression of S100a9 protein by administering the foregoing shRNA into mammalian cells including human cells, or in vitro established mammalian cell-lines.

A still further object of the present invention is to a method for prevention or treatment of dementia by administering the foregoing shRNA to a mammal such as the human.

In order to accomplish the foregoing purposes, the present invention provides a pharmaceutical composition for prevention or treatment of dementia, which includes shRNA having a nucleotide sequence defined by SEQ. ID No. 1 or 2.

The present invention also provides a method of inhibiting expression of S100a9 protein by administering the foregoing shRNA into cells.

The present invention further provides a method for prevention or treatment of dementia by administering the foregoing shRNA to a mammal such as the human.

According to the present invention, shRNA having a nucleotide sequence defined by SEQ. ID 1 or 2 efficiently inhibits expression of S100a9, thereby preventing or treating dementia.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings, in which like reference symbols indicate the same or similar components, wherein:

FIGS. 1A-1C shows S100a9 derived from brains of CT-Tg, Tg2576 mice and patients with human Alzheimer's disease, wherein FIG. 1A is mRNA levels of S100a9 in hippocampus and cortex, relative to loading controls of actin and tublin, FIG. 1B is standardized values of FIG. 1A, and FIG. 1C illustrates immune responses of S100a9 in cortex and hippocampus;

FIGS. 2A-2F illustrates S100a9 expression derived from BV2 cells by amyloid beta and CT, wherein FIG. 2A is immunostaining results of S100a9 (green) and 0311 (red), FIG. 2B is mRNA levels of S100a9, FIG. 2C is measured results of luciferase activity after CT is transfected with a human S100a9 promoter in pGL3 vector while wtAPP and swAPP are transfected with pcDNA vector, FIG. 2D is mRNA levels with respect to concentration, FIG. 2E is measured results of luciferase activity according to the same procedure as of FIG. 2C, and 2F demonstrates S100a9-positive cells visualized with FITC (green)-conjugated secondary antibodies after BV2 cells grown on a glass coverslip are treated with CT (5 mM and 10 mM) and Aβ (20 mM) for 48 h, wherein nuclei are counterstained with DAPI (blue). Scale bars represent 20 mm.

FIGS. 4A and 4B illustrates inhibitory effects of S100a9 expression by all of five (5) types of shRNAs and each of the same, respectively;

FIGS. 6A-6D illustrates results of decreasing amyloid plaques in a brain of Hippocampus (Hippo) and Cortex of Tg2576 mouse by S100a9 knockdown, wherein FIG. 6A is immunostaining results using 6E10 antibody in order to detect amyloid plaques; FIG. 6B is the number of amyloid plaques counted in each group of FIG. 6A; FIG. 6C shows a size and a density of amyloid plaques measured via a multi-gauge program; and FIG. 6D is protein contents measured in separate sites FIG. 6A and hippocampus FIG. 6B by Western-blotting.

DETAILED DESCRIPTION OF THE INVENTION

Figure 1A:
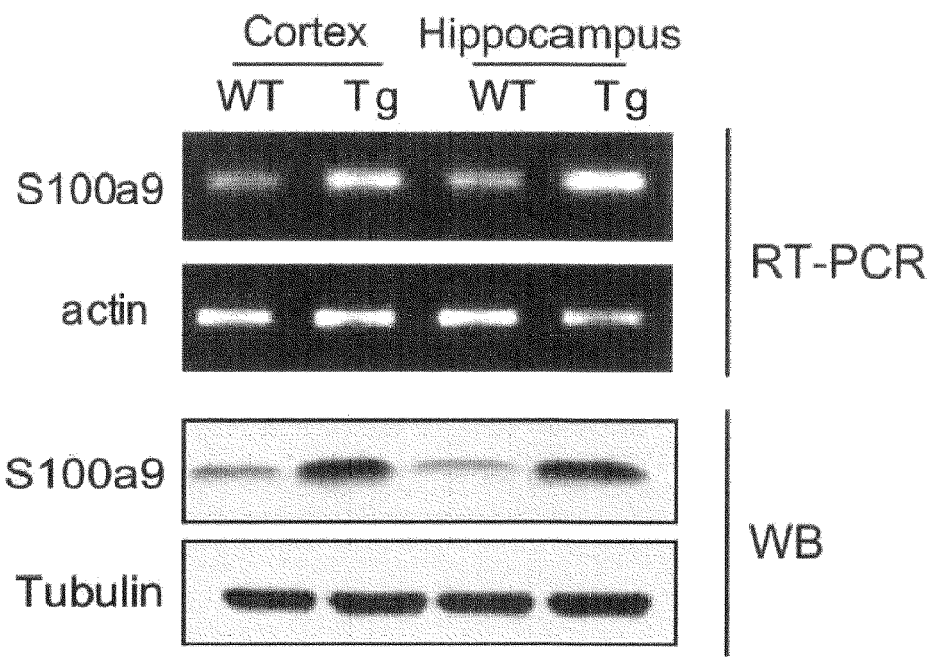

Hereinafter, preferred embodiments of the present invention will be described in more detail through the following examples, in conjunction with accompanying drawings.

According to an exemplary embodiment of the present invention, there is provided a composition for treating dementia, comprising shRNA to inhibit expression of S100a9. More particularly, described herein are: a pharmaceutical composition for prevention or treatment of dementia, which comprises shRNA having a nucleotide sequence defined by SEQ. ID No. 1 or 2 wherein the nucleotide sequence is complementarily bonded to mRNA of S100a9 in order to inhibit expression of S100a9; a method of inhibiting expression of S100a9 protein, comprising administering the foregoing shRNA to cells (mammalian cells including the human cells or in vitro established mammalian cells); and a method for prevention or treatment of dementia by administering the shRNA to mammalian cells such as the human cells.

The present invention will be described in detail below.

The expression "shRNA" refers to a short double-stranded chain wherein a loop is cut into the chain by a dicer and the chain, like siRNA, reacts with RICS so as to express RNAi phenomenon. RNA consists of a stem-loop structure, wherein a long RNA having 19 to 29 nucleotides produces a pair of bases at both sides of the loop site having 5 to 10 nucleotides, thus forming the double-stranded stem. In general, shRNA undergoes in vivo transcription by Pol III promoter and is synthesized, followed by cutting the synthesized shRNA loop using a dicer, and reacting the cut chains with RISC, like siRNA.

The inventive shRNA comprises an anti-sense base sequence defined by SEQ. ID No. 1 or 2, wherein S100a9 expression may be efficiently inhibited by such a sequence. The base sequences defined by SEQ. ID Nos. 1 and 2 are shown in TABLE 1:

TABLE 1

| Sequence No. | DNA Base sequence |
|---|---|
| 1 | CCGGGCTGAGCTTTGAGGAGTGTATCTCGAGATACA CTCCTCAAAGCTCAGCTTTTTG |
| 2 | CCGGCTGATGGCAAAGTTGATCTTTCTCGAGAAAGA TCAACTTTGCCATCAGTTTTTG |

According to one embodiment of the present invention, in order to reduce S100a9 expression, a lentivirus vector encoding the anti-sense base sequence defined by SEQ. ID No. 1 or 2 is provided. Such a system enables more stable and continuous expression of siRNA for a long period of time.

A process of preparing shRNA and introducing the same into a cell or an animal may depend on cell-biological performances of target gene products and/or purposes of experiments, and all of siRNAs or shRNAs in association with S100a9 gene should not always inhibit expression of proteins with physiologically important effects. For instance, among five types of shRNAs (shRNA90, shRNA168, shRNA204, shRNA255 and shRNA280) regarding S100a9, shRNA255 (SEQ. ID No. 1) and shRNA280 (SEQ. ID No. 2) only have efficiently inhibited S100a9 expression, as described below.

In the present description, "dementia" refers to all brain and nervous system diseases developed by expression of S100a9 gene and means complicated clinical syndromes wherein a brain undergoes organic damage or degradation, in turn causing deterioration in cognitive functions such as intelligence, learning, language, etc., as well as deterioration in advanced mental functions. Such diseases may include, although are not restricted to, neuro-degenerative disorders such as: Alzheimer's disease; Parkinson's disease; senile dementia; prion disease; Lewy body dementia; Huntington's disease; Creutzfeldt-Jakob disease, and the like.

Furthermore, the present invention may provide a method of inhibiting expression of S100a9 protein in mammalian cells such as human cells or in vitro established mammalian cell-lines, comprising administering the foregoing shRNA into the cells, as well as a method for prevention or treatment of dementia comprising administering the foregoing shRNA to cells.

The administering process of the shRNA to the cell is to introduce a lentivirus vector containing the inventive shRNA sequence into the cell and may include any conventional methods used by persons skilled in the art. The foregoing cell may be a mammalian cell such as the human cell.

In the present description, "gene" may refer to an encoded nucleic acid molecule relative to a specific protein or, occasionally, mean a functional or structural RNA molecule.

In the present description, "vector" refers to a nucleic acid molecule transportable to another nucleic acid linked thereto. "Lentivirus vector" means a vector extracted from lentivirus (that is, specific shared-nucleotide sequence in lentivirus).

Preferred embodiments of the present invention will be described by the following examples. However, these examples are provided for illustrative purposes but are not construed to restrict the scope of the present invention as defined by the appended claims.

EXAMPLES

Experimental Example 1

RT-PCR

Using a trizol reagent (invitrogen), Total RNA was extracted from brain tissues or cells. The RNA was bound with an oligo-primer (dT) and, using a reverse transcriptase (RT) (AccuPower RT premix, Pioneer), cDNA was prepared. The prepared single-stranded cDNA was used as a target of polymerase chain reaction (PCR) and an annealing temperature was adjusted according to properties of the primer. More particularly, a temperature control cycle comprising 95° C. for 1 minute, 58° C. for 1 minute and 72° C. for 1 minute was executed 30-40 times.

The used primer was S100a9 forward, 5'-CAGCATAAC-CACCATCATCG-3' (SEQ ID NO: 3) reverse, 5'-GTCCTG-GTTTGTGTCCAGGT-3' (SEQ ID NO: 4) actin forward, 5'-CCAGATCATGTTTGAGACCT-3' (SEQ ID NO: 5) reverse, 5'-GTTGCCAATAGTGATGACCT-3' (SEQ ID NO: 6). Electrophoresis of PCR product was conducted in 1.2% Agarose gel. From a band obtained by staining the product with Ethidium Bromide (EtBr), homeostatic mRNA level was scanned using a densitometer and the obtained result was compensated using actin.

Experimental Example 2

Primary Antibody

The following antibodies were used in the present experiment: Anti-APP C-terminal polyclonal antibody (C9) (Chemicon, California), 6E10 (Chemicon), CD11b (Chemicon), IL-1β (R&D), TNF-α (R&D), iNOS (Santa Cruz), anti-S100a9 (R&D), anti-GAPDH (Santa Cruz), anti-tubulin (Santa Cruz), Neprilysin (alpha diagnostic).

Experimental Example 3

Western Blot Analysis

After a human brain cell with dementia and a transformed mouse brain cell were dissolved in an RIPA buffer containing a protease inhibitor (Roche), the prepared mixture was precipitated in a centrifuge at a desired speed for 10 minutes and the supernatant was collected to conduct protein assay (or determine protein concentration). For electrophoresis, each protein with a constant concentration (30 ug to 60 ug) was boiled together with a sample buffer, followed by conducting SDS-PAGE under denaturing conditions. The protein was transferred to a PVDF membrane (Amersham Pharmacia) and blocked using a 5% skimmed milk solution, followed by washing with 0.05% Tween20-TBS three times. Using an antibody associated with a desired protein, the product was incubated for 2 hours. Then, after binding the incubated product with a HRP-polymer secondary antibody (Amersham Pharmacia), the same was detected using an enhanced-chemiluminescent detection system (Amersham Pharmacia). Loading a standard marker during electrophoresis, a size of the detected band was determined, thus verifying gene expression.

Experimental Example 4

Measurement of Luciferase Activity 48 hours after CT, wtAPP and/or sweAPP contained in pcDNA vector together with fe65 were transfected with SHSY5Y cells, a human S100a9 promoter contained in pgL3 vector (Dr. Claus Kerkhoff, Muenstet Univ., Germany) was dissolved using a reporter lysis buffer contained in a Luciferase assay system (Promega, WI, USA), Luciferase activity was determined using a Biocouter M1500 luminometer (Lumac, GE Groningen, Netherlands). Protein assay was executed using a Bradford protein assay reagent (Bio-Rad) while Luciferase activity was standardized into a protein assay value.

Experimental example 5

Immunohistochemical Staining

Mice brains and human AD brains in 10% neutral buffered formalin for 48 h were dehydrated and embedded in paraffin. Before immunostaining, slides were deparaffinized in xylene and then dehydrated through graded alcohols to water. The fluorescent immunohistochemistry was performed with appropriate primary antibodies at 4uC for O/N and visualized using Cy3-conjugated or FITC-conjugated secondary antibody (Jackson, West Grove, Pa.). DAPI counter staining was performed. Images were collected using the LSM 510 program on a Zeiss confocal microscope (Carl Zeiss MicroImaging, Inc.). For the non-fluorecence labeling, Immunohistochemistry was performed using a Vectastain avidin-biotin complex (ABC) elite kit. Reaction product was detected using 3,3-diaminobenzidinetetrahydrochloride (DAB). Photomicrographs were acquired with a, color digital camera DFC280 (Leica) attached to a microscope (BX-51; Olympus).

Experimental Example 6

Statistical assay

Statistical assay comprised analysis of variance (ANOVA) executed using a statistical package program (SPSS) (statistical package social science, version 14.0, Chicago, Ill.) and significance test conducted by Duncan's multiple rage test with $p<0.05$ in order to determine significance of test samples.

Example 1

Determination of S100a9 Protein Derived from Alzheimer's Disease

From each of a normal mouse aged 11 months and a mouse with dementia, APPV717I-CT100 Tg, a brain was removed and whole RNA was extracted from a hippocampus site of the brain using trizol (invitgen). Double-stranded cDNA was synthesized from mRNA and hybridized to CodeLink Twin-chip™ Mouse-20K (Amersham Bioscience). All microarray experiments were conducted by Digital Genomics (Seoul, South Korea). A scanned DNA chip was standardized by conventional processes such as image plot, histogram, box plot, RNA degradation plot, scatter plot, MA plot, etc. through a computer program. Genes obtained according to the foregoing procedures were subjected to SAM analysis in order to investigate a genetic origin or functions of gene and, according to clustering of genes showing noticeable fold change or similar genes in terms of functions, genes specifically expressed in the dementia mouse rather than the normal mouse were discovered.

In order to extract gene candidate groups associated with Alzheimer's disease, whole RNAs in hippocampus sites of the CT-Tg mouse and the same aged control mouse were subjected to microarray assay and verified by RT-PCR and Western blotting.

Figure 1B:
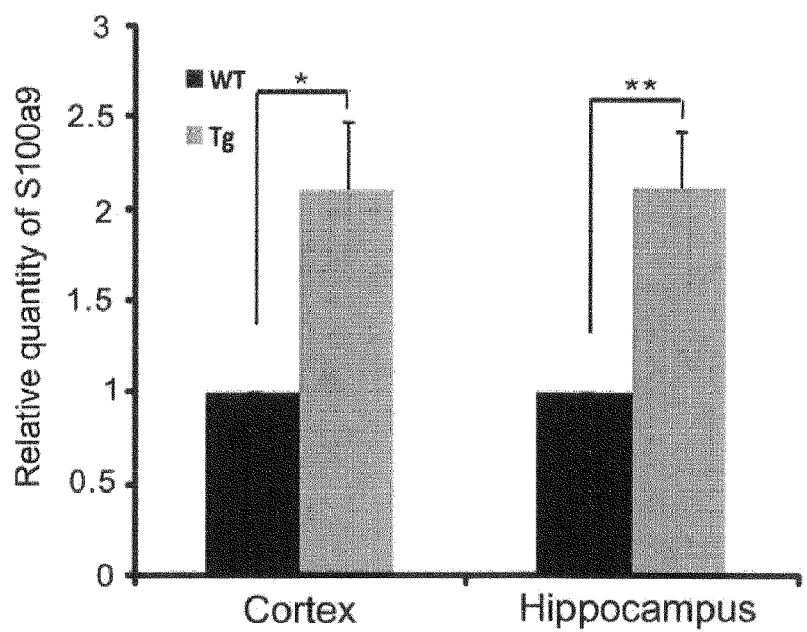
Figure 1C:
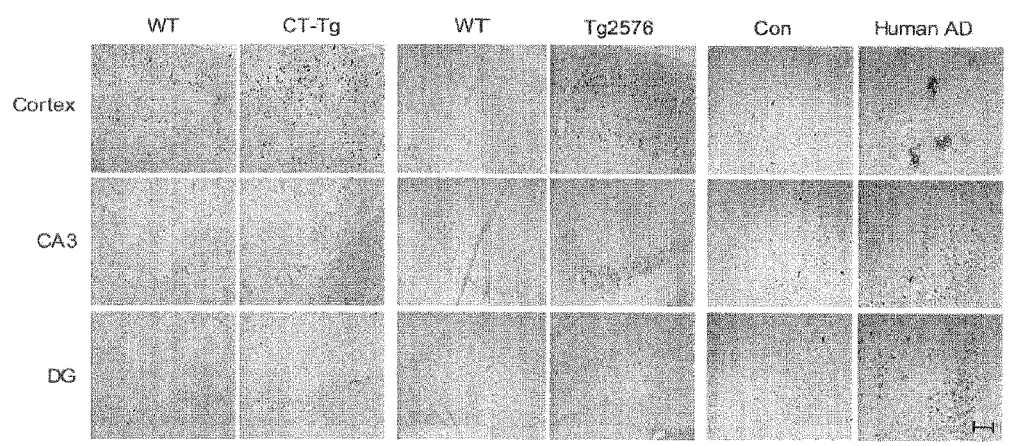

As a result, S100a9 was selected as a gene closely associated with the above disease. As shown in FIG. 1A, mRNA level of S100a9 was derived from hippocampus and cortex sites in the brain of the CT-Ta mouse. From results of western blotting and immunohistochemical assay, it was also identified that S100a9 protein is increased in the hippocampus and cortex sites in the brain of the CT-Tg mouse, compared to the control (FIG. 1). As shown in FIG. 1C, a Swedish type APP over-expressive Tg2576 mouse exhibited considerable increase in S100a9 at the hippocampus and cortex sites of the brain of the above mouse, compared to the control.

For both CT-Tg and Tg2576 mice, in order to examine physiological significance of S100a9, a patient with human Alzheimer's disease and the same-aged control were subjected to assay of S100a9 levels. Brain tissue of a normal person who was 69 to 87 years old, as well as paraffin-fixed brain tissue and lyophilized brain tissue of an Alzheimer's disease patient were obtained from Netherlands Brain Bank (NBB). According to neuro-pathological diagnosis, the brain tissues of the Alzheimer's disease patient were in Braak & Braak stage V or VI while the normal brain tissue was in Braak & Braak stage 0 or 1. For immunohistochemical staining, the hippocampus part was cut into coronal sections with 4 mm. The lyophilized brain tissue was used for western blotting. As shown in FIG. 10, analysis results demonstrated that the brain of the patient with Alzheimer's disease and a whole fused product thereof exhibit increase in expression of S100a9, compared to the control.

Example 2

Figure 2A:
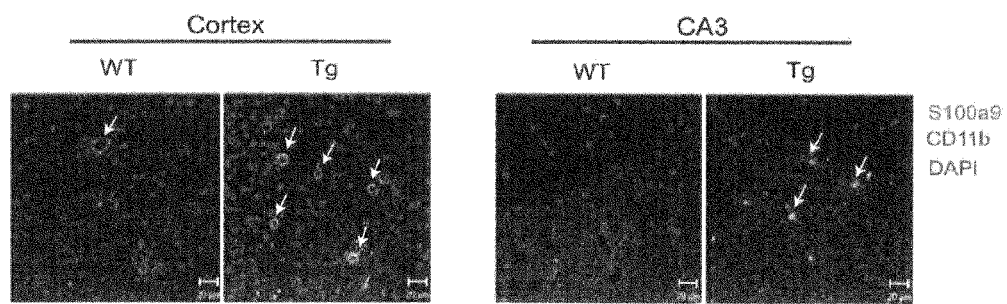

Determination of Expression of Amyloid Beta or Amyloid Precursor Protein in BV2 Cell and Microglia Cell It was identified that S100a9 expression is increased in the brain with Alzheimer's disease as well as CT-Tg and Tg2576 mice, all of which produce amyloid beta or amyloid precursor protein (CT) in large quantities. This relates closely to excessive production of amyloid beta and/or amyloid precursor protein. As to the brain of the CT-Tg mouse used for a gene chip, S100a9 was highly expressed in CD11b-positive microglia (FIG. 2A).

Figure 2B:
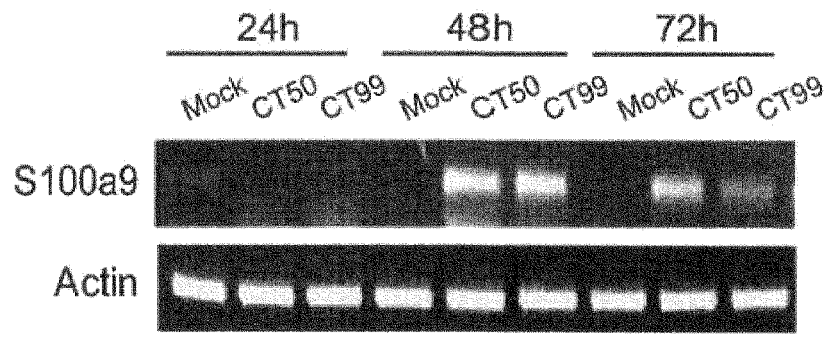

In order to determine whether Alzheimer's disease is associated with a pathological mechanism of S100a9, endogenous expression of S100a9 in BV2 cell as a microglia cell-line was derived. The mouse BV2 cell was incubated with a DMEM medium containing 5% fetal bovine serum (FBS, Hyclone) and 1% antibiotic (100 U/ml/100 µg/ml) (Life Technology) in a 5% $CO_2$ cell incubator at 37° C. After transfection with CT50 or CT99 in murine BV2 microglia cells, gene expression of S100a9 was detected by RT-PCR. As a result, it was found that the mRNA level of S100a9 is considerably increased 48 hours and 72 hours after transfection with CT50 or CT99, especially, 48 hours after transfection (FIG. 2B).

Figure 2C:
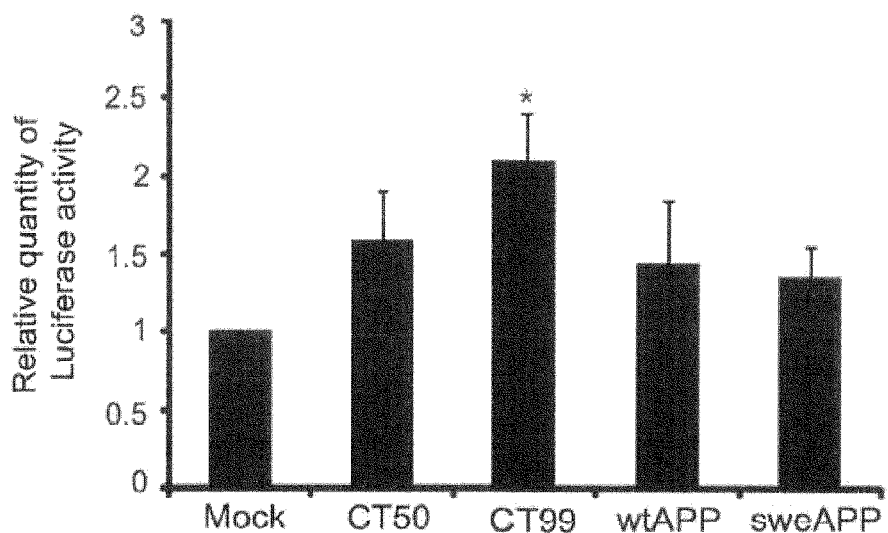
Figure 2D:
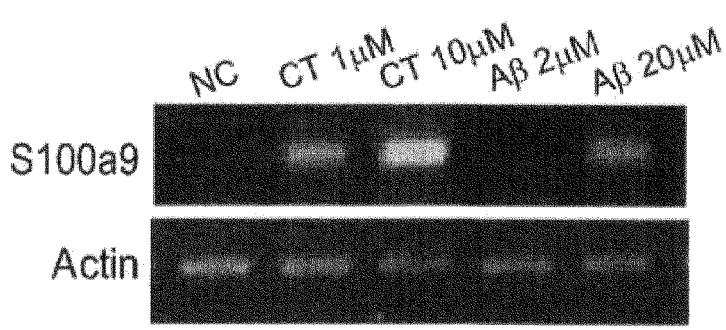
Figure 2E:
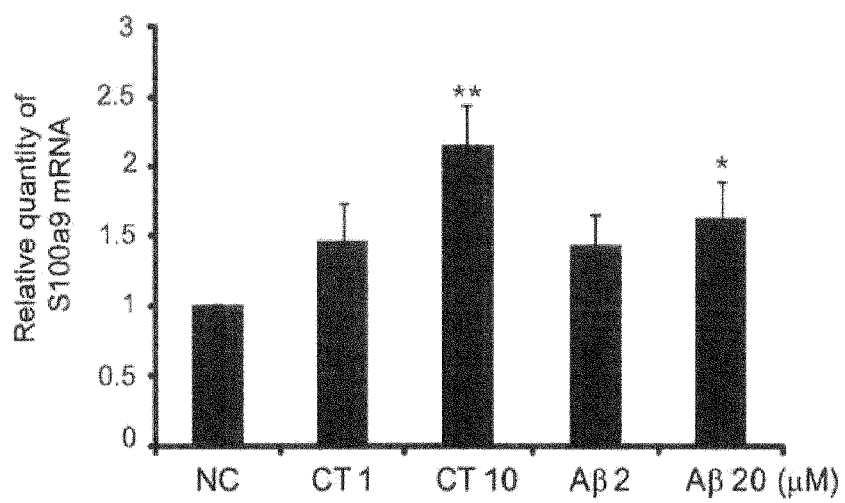
Figure 2F:
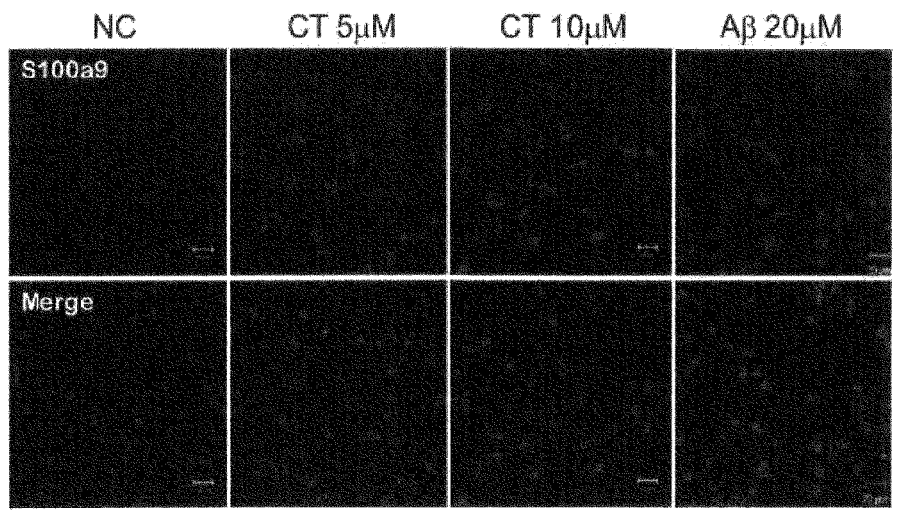

Amyloid beta or amyloid precursor protein can be induced by controlling promoter activity of S100a9. Possibility of such induction was investigated according to promoter activity assay. 48 hours after transfection, transfection effects of CT50 and CT99 upon S100a9 promoter activity were determined (1.58 $\pm$ 0.32 by CT50, 2.09 $\pm$ 0.32 by CT99; FIG. 2C). Effects of normal APP (wtAPP) and Swedish type APP (swe-APP) upon S100a9 promoter activity were also determined (1.43 $\pm$ 0.41 by wtAPP, 1.35 $\pm$ 0.20 by sweAPP) and, in particular, CT99 considerably increased S100a9 promoter activity (FIG. 2C). Subsequently, amyloid beta and amyloid precursor protein peptides were treated at different concentrations (1, 10 mM of CT or 2, 20 mM of Aβ) for 48 hours, in turn inducing concentration-dependent mRNA level of S100a9 (FIG. 2D). 10 mM amyloid precursor protein significantly increased the mRNA level of S100a9. [ratio=2.15$\pm$60.29, p=0.0048 versus NC (negative control), student's t-test] (FIG. 2E). Immunocytochemical analysis also demonstrated that S100a9 is dose-dependently derived by amyloid beta or amyloid precursor protein (FIG. 2F).

Example 3

Evaluation of Effects of S100a9 Derived from Amyloid Beta or Amyloid Protein Precursor Upon Increase in Calcium Content of Cell 48 hours after treatment using amyloid precursor protein or amyloid beta peptides at different concentrations, BV2 cells cultured in a cover glass coated with 10 mg/ml polyethyleneimine (PEI) were washed twice using a Hank's solution (Gibco) and incubated using 10 µM Fluo-3/AM at 37° C. for 20 minutes. After mounting the cells, the cells were subjected to excitation with an Argon ion laser (wavelength ($\lambda$)=488 nm) using a laser-scanning confocal microscope and fluorescence measurement at $\lambda$>515 nm. Change of calcium content $[Ca^{2+}]_i$ in cells was observed and compared with the control. Using 0.1, 1 and 10 mM amyloid precursor protein peptides or 1 and 10mM amyloid beta peptides, BV2 cells were treated for 48 hours and $[Ca^{2+}]_i$ levels thereof were evaluated by a Fluo3/AM method.

$[Ca^{2+}]_i$ level was dose-dependently increased and such a degree of increase was calculated relative to the control. 10 mM amyloid precursor protein significantly increased $[Ca^{2+}]_i$ level. In order to determine whether S100a9 may increase $[Ca^{2+}]_i$ level, S100a9 siRNA (si-S100a9) was treated using BV2 cells already treated with amyloid precursor protein peptides.

Figure 3A:
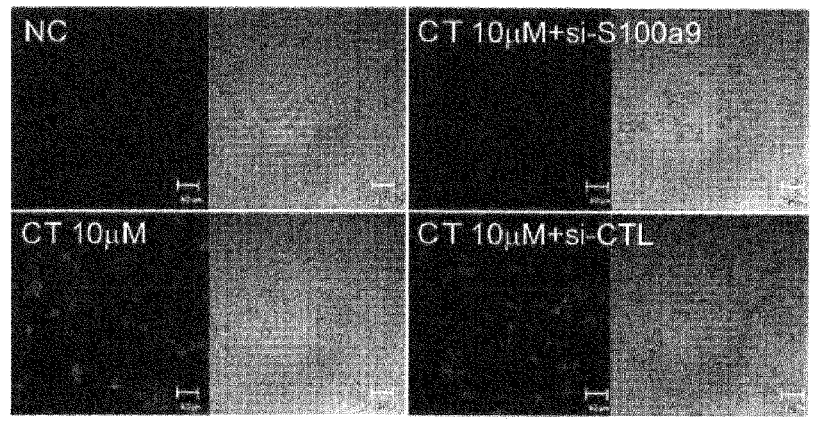
FIGS. 3A-3E illustrates increase in $[Ca^{2+}]_i$ concentration and proinflammatory cytokine of S100a9 derived from BV2 cells by amyloid beta and CT.
Figure 3B:
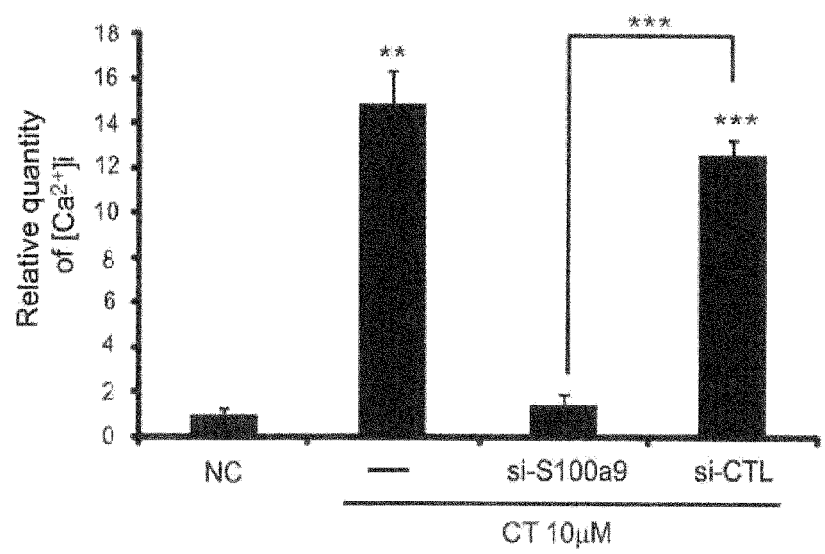
Figure 3C:
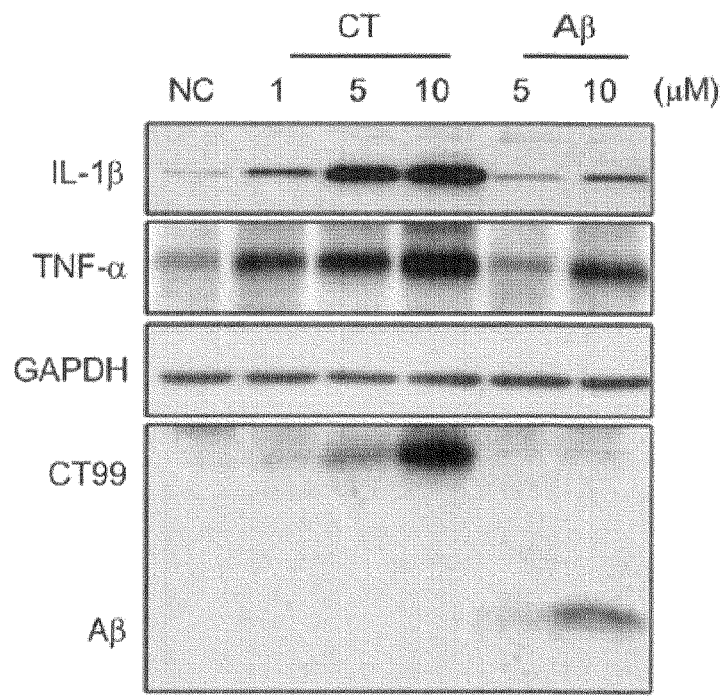

As a result, S100a9 gene knockdown caused decrease in S100a9 expression (FIG. 3D) and significantly reduced increase in $[Ca^{2+}]_i$ level by amyloid precursor protein (from ratio=12.63$\pm$60.65 to ratio=1.49$\pm$60.45, p=0.00016 versus si-CTL/CT 10 mM, Student's t-test). si-CTL did not influence $[Ca^{2+}]_i$ level (FIGS. 3A and 3B). $[Ca^{2+}]_i$ level obtained by amyloid beta treatment and S100a9 gene knockdown during combination of si-S100a9 significantly reduced increase in $[Ca^{2+}]_i$ level by 10 mM amyloid beta (from ratio=3.31$\pm$60.58 to ratio=1.02$\pm$60.20, p=0.0086 versus si-CTL/Ab 10 mM, Student's t-test).

Example 4

Figure 3D:
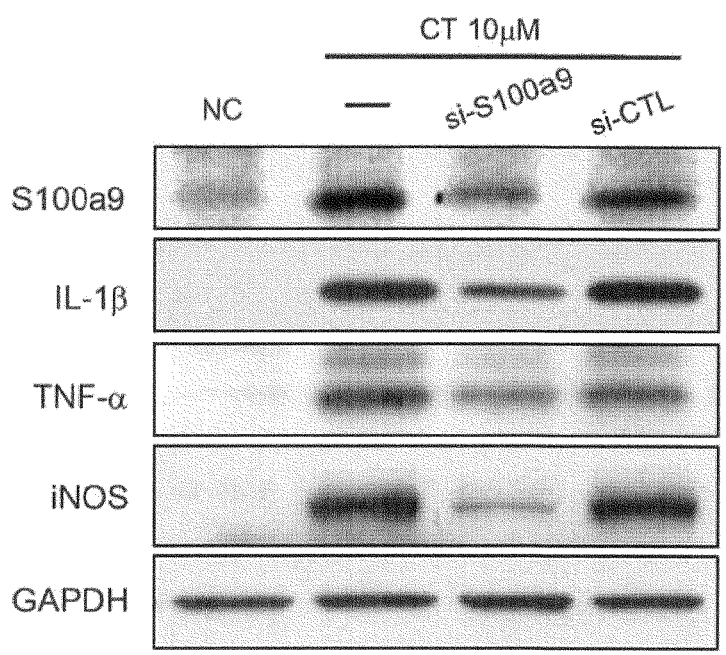

Determination of Increase in Proinflammatory Cytokines by Treatment Using Amyloid Beta or Amyloid Precursor Protein According to the present invention, it was found that treatment using amyloid beta or amyloid precursor protein derives significant and dose-dependent increase in IL-1β and TNF-α as proinflammatory cytokines (FIG. 30). In order to test efficacy of S100a9 induction for production of proinflammatory cytokines, si-S100a9 was used for silencing S100a9. IL-113 and TNF-α levels derived from amyloid precursor protein were reduced to 60% by si-CTL and S100a9 expression was also reduced (FIG. 3D).

Figure 3E:
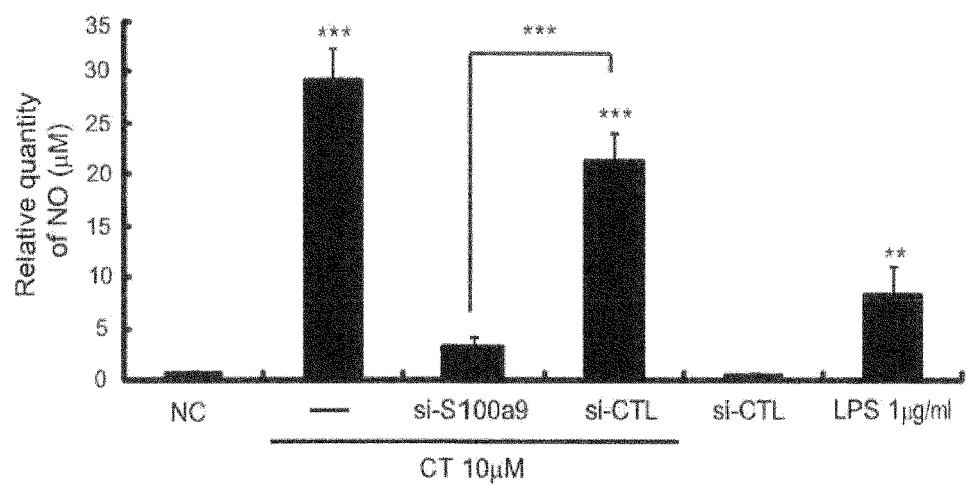

Nitrogen oxide (NO) generation was measured on the basis of $NO_2$ increase/decrease in a cultured solution. After treating BV2 cells incubated in a 96-well plate using amyloid precursor protein peptides, increase in NO content of the cultured solution was measured using a Griess reagent (G4410, Sigma). After admixing the cultured solution with the same amount of Griess reagent and measuring light absorption for 5 minutes at 540 nm in a spectrophotometer, the obtained results were analyzed, compared to those of the control. According to the results, it was found that iNOs level increased by the amyloid precursor protein was reduced to 70% by si-S100a9 (FIG. 3D). As shown in FIG. 3E, silencing of S100a9 gene significantly inhibited release of amyloid precursor protein-derived NO from 21.2962.78 (mM) to 3.1960.88 (mM).

Example 5

Determination of Decrease in Impairment of Learning and Memory of Tg2576 Mouse by S100a9

For investigation of S100a9 function to Alzheimer's disease, a short hairpin RNA (sh-S100a9) and a short hairpin RNA of lentivirus (sh-CTL) as a control were injected into each brain of a 13 week old Tg2576 mouse and a normal mouse, respectively. Five types of shRNAs (sh-S100a9) were prepared as shown in TABLE 2 below:

TABLE 2

| Sh S100a9 | |
|---|---|
| Sh90 | CCGGCTTCCATCAATACTCTAGGAACTCGAGTTCCTAGAGTAT TGATGGAAGTTTTTG (SEQ ID NO: 7) |
| Sh168 | CCGGGTTGGCAACCTTTATGAAGAACTCGAGTTCTTCATAAAG GTTGCCAACTTTTTG (SEQ ID NO: 8) |
| Sh204 | CCGGCTGATGGCAAAGTTGATCTTTCTCGAGAAAGATCAACTT TGCCATCAGTTTTTG (SEQ ID NO: 9) |
| Sh255 | CCGGGCTGAGCTTTGAGGAGTGTATCTCGAGATACACTCCTCA AAGCTCAGCTTTTTG (SEQ ID NO: 10) |
| Sh280 | CCGGCTGATGGCAAAGTTGATCTTTCTCGAGAAAGATCAACTT TGCCATCAGTTTTTG (SEQ ID NO: 11) |

From results of inhibiting S100a9 expression by the prepared shS100a9s, it was demonstrated that sh255 and sh280 can efficiently inhibit S100a9 (FIG. 4). Especially, sh255 was selected and transfected to HEK293T cells together with a transfer vector plasmid (sh-CLT or sh-S100a9) and a packaging construct plasmid pCMVΔR8.2, envelope plasmid pVSV-G, thus creating viral particles. After incubation overnight, the culture solution was changed and collected after 2 to 4 days, followed by filtering the collected solution using a filter with a pore size of 0.45 mm and centrifuging the same at 35,000 rpm for 2 hours. The treated product was dissolved again in PBS to yield viral particles. As for in vivo experiment, centrifugation at 50,000 rpm and 4° C. for 2 hours was further conducted to form a concentrate with 1,000 times concentration. The concentrate was used for in vivo experiment.

An APPswe Tg2576 mouse was purchased from Taconic Farms (Germantown, N.Y.) and, according to information of the provider, inbreeding was performed by mating the purchased mouse with a C57B16/SJL F1 female mouse. 13 month old Tg2576 mice (Tg) and age controls (WT) were separated into 4 groups, respectively, each of which consists of 8 mice. To a WI or Tg group, 2 ml of concentrated sh-CTL or sh-S100a9 255 viral particles was injected into hippocampus sites (AP, 0.18 mm; ML, 0.20 mm; DV, 0.19 mm) of the brain, using a Kopf stereotaxic frame (Kopf Instruments, Tujunga, Calif.).

After 2 months, the sh-S100a9 255 mouse or the sh-CTL mouse was subjected to Morris Water Maze task to evaluate impairment of learning and memory thereof.

Such Morris Water Maze task for evaluating spatial memory of laboratory animals is in general performed by filling a circular water bath (diameter of 140 cm and height of 45 cm) with water (23° C.) to a height of 30 cm, placing an escape platform with a diameter of 10 cm in one quadrant of the water bath in order to be positioned lam below the water surface, and dispersing skimmed milk thereto, enabling the escape platform not to be visible. On 1 day of the experiment, an experimental animal freely swam in the water bath for 60 seconds without the platform. By allowing the animal to swim three times every day for five days but in different quadrants of the water bath, cognitive adaptation training was performed. When the experimental animal reached the escape platform, the animal was allowed to stay there for 30 seconds. In a case where the animal did not find the escape platform within. 60 seconds, memory induction was executed by placing the animal on the platform for 30 seconds. The animal was allowed to rest the day after completion of all trainings and, on 7 day, the platform was removed and a probe test was conducted to record escape latency, enabling evaluation of working memory.

Figure 5A:
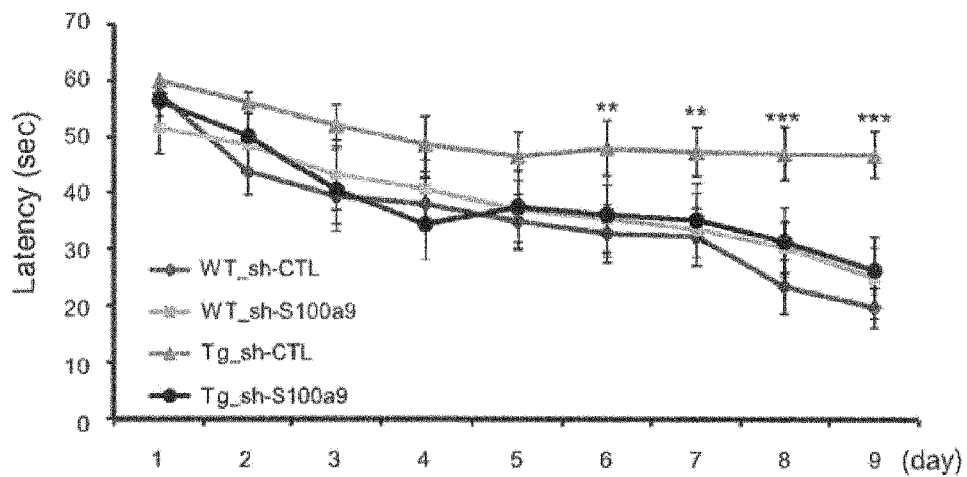
FIGS. 5A and 5B illustrates decrease of impairment in learning and memory in Tg2576 mouse by treatment using shS100a9 255.
Figure 5B:
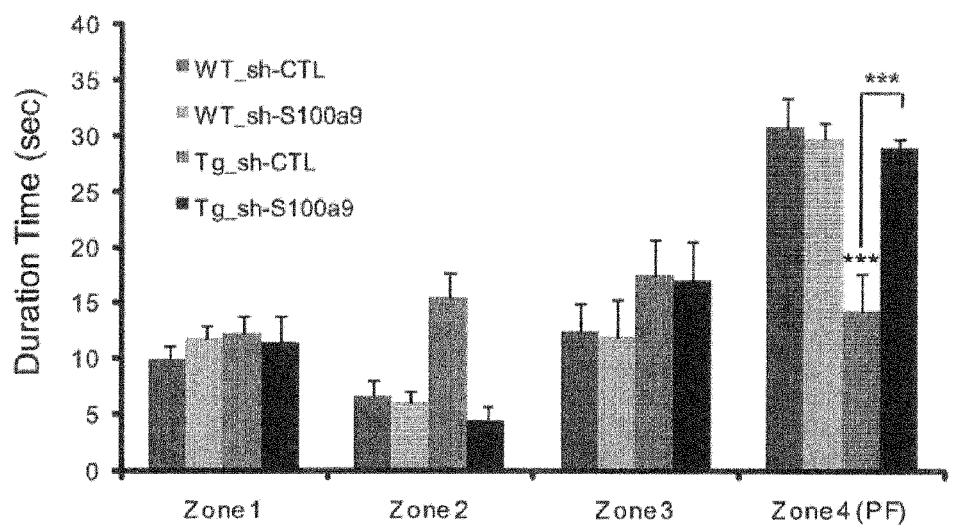

As a result, the Tg2576 mouse (Tg_sh-S100a9) containing sh-S100a9 255 exhibited distinguishable difference in learning aspect at day 6, compared to the Tg_sh-CTL control (p=0.0055, F=4.49; FIG. 5A). On the other hand, WT_sh-CTL and WT_sh-S100a9 groups did not have substantial difference therebetween (FIG. 5A). As to the Tg2576 mouse, in order to determined improvement of impaired memory by sh-S100a9 255 injection, a probe test was carried out 48 hours after the final injection and a stand time of the animal in the fourth quadrant of the water bath without the platform was recorded. Similar to WT, the Tg_sh-S100a9 255 exhibited a considerably longer stand time in the fourth quadrant than the other quadrants (first to third quadrants). On the other hand, the stand time in each of the other quadrants was substantially similar to that of the Tg_sh-CTL. In addition, WT mice treated with sh-S100a9 255 and sh-CTL, respectively, did not show remarkable difference therebetween (FIG. 53). From the foregoing results, it is believed that S100a9 knockdown in Tg2576 mouse increases spatial memory.

Example 6

Reduction of Amyloidal Senile Plaque and Eosinophilic Pyknotic Neurons in Tg2576 Mouse by sh-S100a9

In order to investigate potential association between memory impairment and amyloid deposition, 15 week old WT_sh-CTL, WT_sh-S100a9 255, Tg_sh-CTL and Tg_sh-S100a9 255 mice were subjected to measurement of amyloidal senile plaques as well as amyloid beta and amyloid precursor protein levels, using 6E10 amyloid beta capable of specifically recognizing 1 to 17 amino acids in the amyloid beta site, after behavior test thereof.

After paraffin removal and hydration, the treated brain tissue was stained using Congo Red at a concentration of 0.4% (w/v, Sigma) at room temperature for 10 minutes, washed with water, stained again using hematoxylin for 1 minute and washed with water, followed by dehydrating the tissue in 50 to 100% alcohol solution, washing the same with xylene, and mounting the washed tissue using a permounting solution (Fisher Scientific) in order to observe the tissue by a microscope.

Figure 6A:
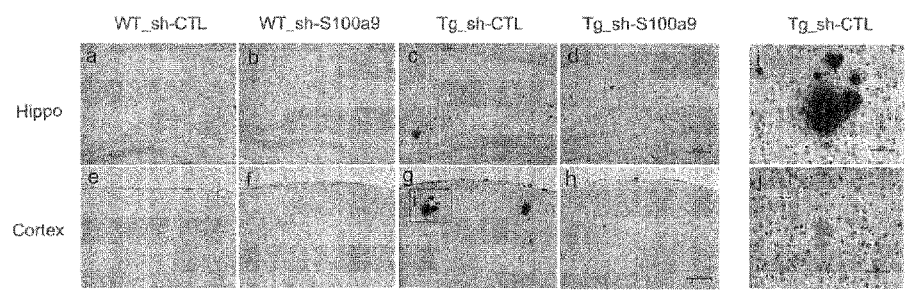
Figure 6B:
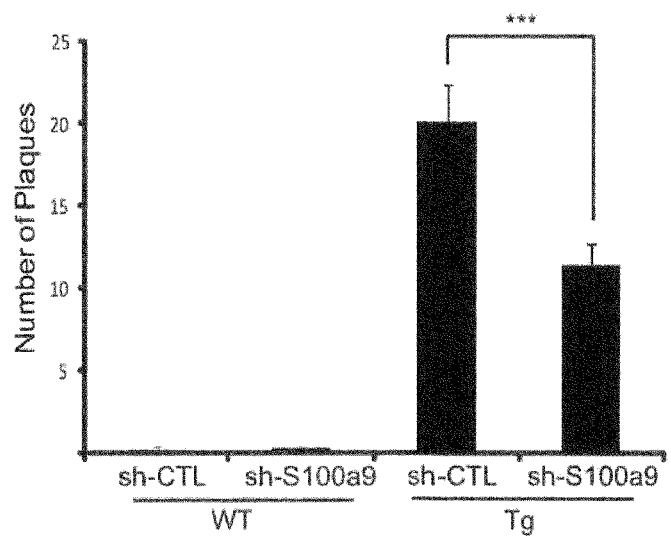

The amyloidal senile plaques were well stained in the cortex and hippocampus sites by 6E10 antibody (FIG. 6A). Dense-core plaques were detected in the brain of the Tg_sh-CTL group. However, the number of amyloidal senile plaques in the Tg_sh-S100a 255 group was drastically reduced (20.1562.24 to 11.461.34, p=0.001, Student's t-test; FIG. 6B). For WT mouse, amyloidal senile plaques were little observed in the brain (FIGS. 6A and 6B).

Figure 6C:
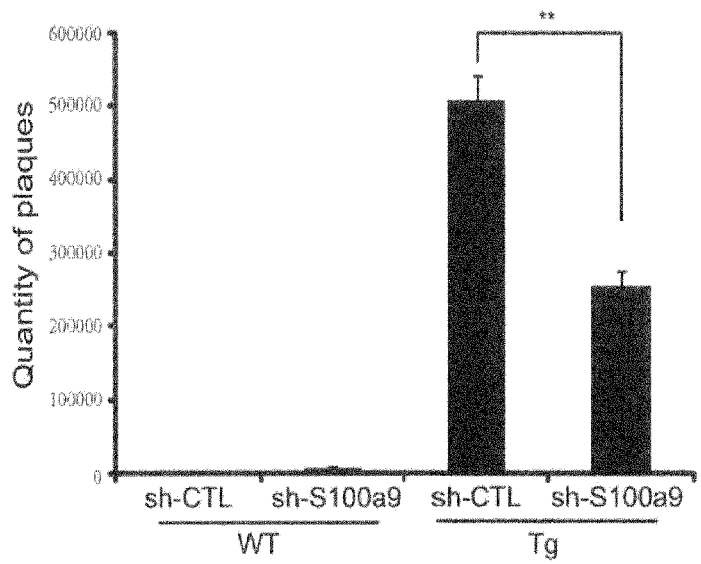

The foregoing data were obtained by quantitative determination of a size and a density of the amyloidal senile plaques (FIG. 6C). In order to detect the amyloidal senile plaques, Congo Red staining was executed and the amyloidal senile plaques stained with Congo Red were substantially identical to amyloid beta immunoreactive plaques (FIG. 6A).

Figure 6D:
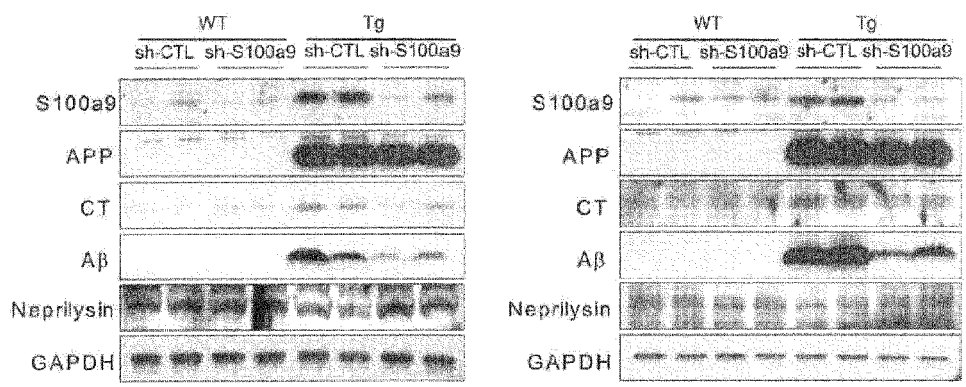

Brain parts were labeled using S100a9 antibody. Lentivirus sh-S100a9 remarkably reduced S1009 in Tg_sh-S100a9. S100a9 expression in cortex and hippocampus of the brain of each mouse group was increased in the Tg_sh-CTL mouse but decreased in the Tg_sh-S100a9 mouse, compared to the WT mouse. In contrast, the WT_sh-CTL and WT_sh-S100a9 mice did not show substantial difference in S100a9 expression therebetween (FIG. 6D).

APP expression was not varied between Tg_sh-S100a9 255 and Tg_sh-CTL mice, amyloid beta and amyloid precursor-protein levels were decreased in Tg_sh-S100a9 255 (FIG. 6D) and substantially identical to the reduced number of amyloidal senile plaques (FIGS. 6A to 6C). Such results demonstrated that S100a9 is a factor increasing a content of the amyloid beta and amyloid precursor protein in the Tg2576 mouse.

As for amyloid beta neprilysin, effects of S100a9 were determined and expression of the neprilysin in the brain of each mouse group was measured. The neprilysin level in the Tg2576 mouse was decreased by about 40%, compared to the same aged WT mouse. However, the neprilysin level in Tg_sh-S100a9 255 mouse was substantially similar to that of a normal (WT) mouse with the same age (FIG. 6D). Eosinophilic Pyknotic Neurons (EPNs) showing degeneration of neurons were observed using hematoxylin and eosin (H&E) staining.

A slide containing brain tissue was treated by staining it using Mayer's hematoxylin (DakoCytomation) and an eosin (Acros organics) solution and dehydrating the tissue in an alcohol solution at different concentrations, was washed using xylene and mounted using a Canadian balsam solution, so as to observe the tissue using a microscope.

Among brain parts of the Tg_sh-S100a9 mouse, the number of EPNs was decreased in the cortex and hippocampus sites. However, EPNs were not substantially discovered in WT_sh-CTL and WT_sh-S100a9 groups. Such results demonstrated that S100a9 influences neuro-degeneration in the Tg2576 mouse as; an Alzheimer's disease model.

What is claimed is:

1. A pharmaceutical composition for treatment of dementia, comprising an shRNA sequence defined by SEQ ID NO: 1 or SEQ ID NO: 2.

2. A method for inhibiting expression of s100a9 protein, comprising administering a nucleotide sequence to a cell, wherein the nucleotide sequence is the sequence of SEQ ID NO: 1 or SEQ ID NO: 2.

3. The method according to claim 2, wherein the cell is a mammalian cell including a human cell or in vitro established mammalian cell-line.

4. A method for treatment of dementia comprising administering an shRNA defined by SEQ ID NO: 1 or SEQ ID NO: 2 to a mammal except for a human, wherein the nucleotide sequence complementarily binds to mRNA of S100a9 so as to inhibit expression of S100a9.

5. A method for treatment of dementia comprising administering an shRNA defined by SEQ ID NO: 1 or SEQ ID NO: 2 to a cell, wherein the nucleotide sequence complementarily binds to mRNA of S100a9 so as to inhibit expression of S100a9.

6. The method according to claim 5 wherein the cell is a mammalian cell, including a human cell, or an in vitro established mammalian cell-line.

* * * * *